United States Patent [19]

Koopman et al.

[11] 4,370,418
[45] Jan. 25, 1983

[54] LIQUID LEVEL CONTROL BY SUBSURFACE DRAW OFF

[75] Inventors: Benjamin L. Koopman, Gainesville, Fla.; Antonio O. Lau, Morristown; Peter F. Strom, Highland Park, both of N.J.; David Jenkins, Kensington, Calif.

[73] Assignee: University of California, Berkeley, Calif.

[21] Appl. No.: 286,372

[22] Filed: Jul. 24, 1981

[51] Int. Cl.³ .............................................. C12M 1/36
[52] U.S. Cl. ..................... 435/289; 435/3; 435/141; 137/393; 137/590; 422/106
[58] Field of Search ....................... 435/3, 141, 289; 422/184, 106, 225; 137/393, 590

[56] References Cited

U.S. PATENT DOCUMENTS

| | | | |
|---|---|---|---|
| 1,020,642 | 3/1912 | Elkofer | 137/393 |
| 2,983,311 | 5/1961 | Anders | 137/590 X |
| 3,233,448 | 2/1966 | Brown | 73/53 |
| 3,797,702 | 7/1957 | Martin | 137/392 |
| 3,847,749 | 11/1974 | Smith et al. | 435/289 X |
| 4,029,584 | 6/1977 | Takemoto | 137/590 X |
| 4,124,137 | 11/1978 | Hesse et al. | 137/590 X |

OTHER PUBLICATIONS

Biotechnology and Bioengineering, vol. XXII, pp. 2433–2435, 1980 (11/80 Issue), Koopman et al.

Primary Examiner—Ferris H. Lander
Attorney, Agent, or Firm—Phillips, Moore, Lempio & Finley

[57] ABSTRACT

Liquid (13, 13a) within a vessel (12, 12a) which receives an inflow is maintained at a predetermined level (43) by discharging liquid as necessary to compensate for the inflow. Discharge flow is drawn from below the surface (18) of the liquid to avoid clogging from scum or from other undesirable effects of surface draw off. Intake structure (34) for the discharge pump (33, 33a) has a branched flow path (47) that includes a first inlet (48) situated above the predetermined level, a second inlet (49) situated below the predetermined level and a flow junction (51) through which both inlets are communicated with the discharge pump, the junction being at the predetermined liquid level. If the liquid rises above the flow junction, the pump draws liquid through the second, subsurface inlet. If the liquid surface recedes below the flow junction, the pump aspirates air or other gas through the first inlet. Consequently liquid level is stabilized at the elevation of the flow junction. The system is applicable, for example, to chemostats (11, 11a) in which microorganisms are cultured in a liquid medium.

10 Claims, 5 Drawing Figures

FIG_1

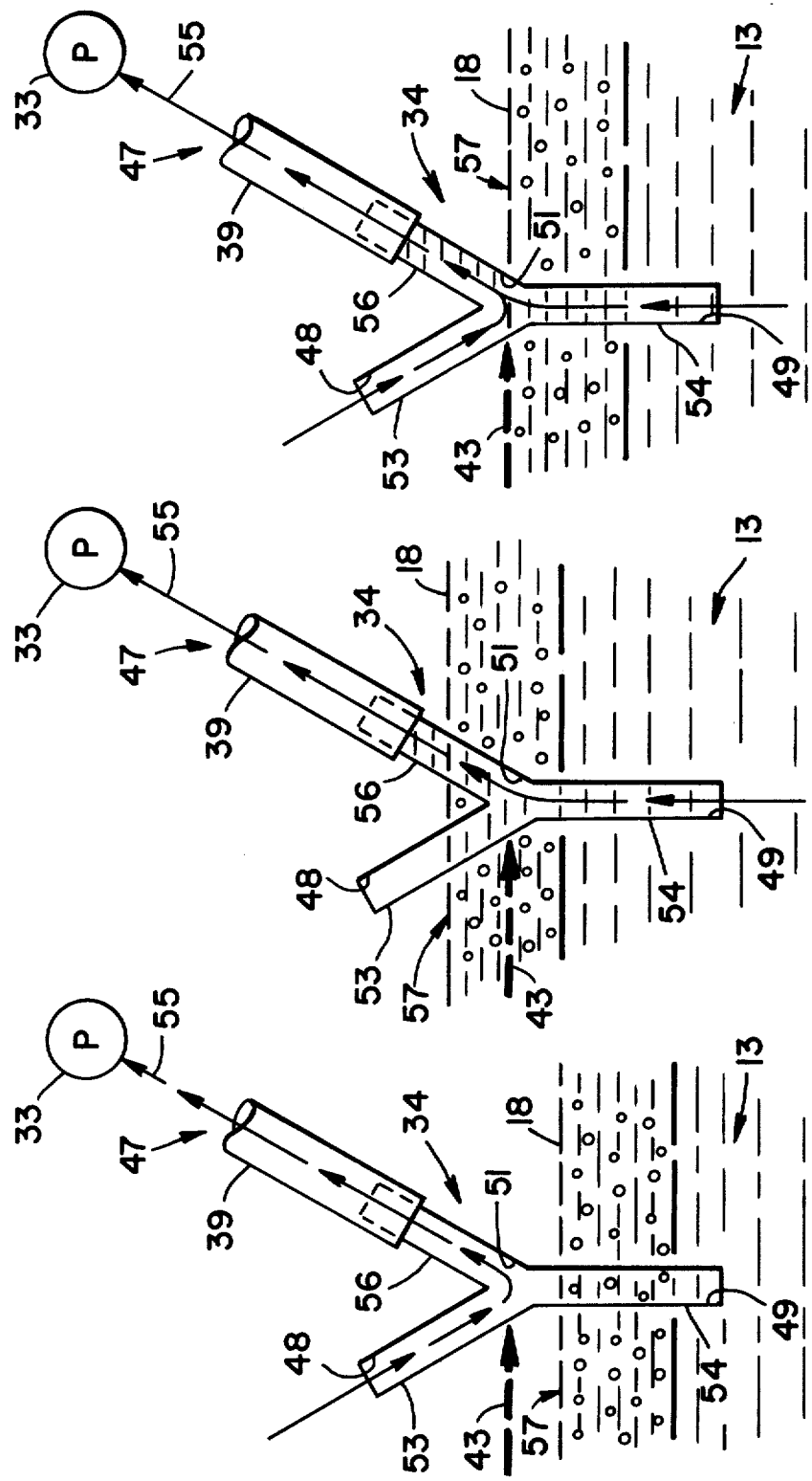

LIQUID LEVEL CONTROL BY SUBSURFACE DRAW OFF

The Government has rights in this invention pursuant to Grant No. CME-7684422 awarded by the National Science Foundation.

TECHNICAL FIELD

This invention relates to liquid level control in fluid containing systems and more particularly to apparatus such as chemostats in which a controlled discharge of subsurface liquid from a vessel is required to compensate for an inflow.

BACKGROUND OF THE INVENTION

Level controls are used in many fluid systems to maintain the volume of liquid in a tank or other containment vessel substantially constant. In instances where the tank or the like receives an inflow of liquid, the level control operates by establishing a matching discharge flow. In certain systems of this kind it is desirable that the discharge flow be drawn from below the surface of the liquid. Thus the desired liquid level cannot be maintained by simply providing an overflow passage or drain opening in the wall of the vessel at the desired liquid level.

Chemostats for culturing microorganisms in a liquid medium are one example of such systems. Maintenance of the microbial culture usually requires a continuous or at least periodic inflow of liquid medium to the chemostat vessel. A matching controlled discharge flow of liquid from the chemostat tank is required to avoid overflow and to maintain the culture volume constant. It is not usually practical to accomplish this by simply pre-establishing matched fixed inflow and outflow rates. Even a slight imbalance in the initial adjustment or an imbalance which arises in the course of operation from any of various possible causes will, over an extended period of time, result in a significant rise or fall of liquid level in the chemostat. Thus as a practical matter the liquid discharge components must include some arrangement for varying the outflow when necessary to maintain a precise balance with inflow.

A surface layer of scum, foam or other floating matter may form on the chemostat liquid. Thus it is desirable that the discharge flow be drawn from a level below the surface of the liquid. This reduces clogging in the discharge flow path and also provides an effluent having a composition representative of the bulk of the liquid medium within the chemostat and which is more useful for analysis than a sample taken from the atypical surface layer.

Prior chemostat liquid level controls that provide for subsurface draw off often rely on an inverted siphon or, alternately, have a discharge pump or solenoid operated pinch valve controlled by a level sensor probe that is typically electrical in part. Each of these types of prior level control is subject to significant problems and disadvantages.

An inverted siphon in this context requires that an opening be made in the chemostat vessel wall at or below the desired liquid level. Chemostat tanks are typically formed of glass and are thus difficult to perforate. Further, the junction between the wall and siphon tube is prone to breakage and in some cases to leakage and the protruding tube may interfere with operations to be performed or other apparatus in the vicinity. Because the discharge flow of a siphon is generated by gravity, it tends to be less forceful than is desirable and such siphons are prone to clogging.

Consequently, the systems which use a pump or solenoid controlled valve and electrical liquid level probe have usually been considered to be the preferred type. Performance requirements for these instruments are frequently severe. In many cases, the probe must withstand repeated autoclaving. Operation under either aerobic or anaerobic conditions may be required and the probe must accurately sense liquid level even in the presence of foam, scum or other floating material. Electrical probes for such usage are very costly and may have adverse effects. In one instance, for example, use of an electronic liquid level probe was found to induce extensive electrolytic corrosion of submerged stainless steel elements in a chemostat tank which in turn released toxic hexavalent chromium into the bacterial culture.

Thus a more reliable and trouble free form of liquid level control would be highly advantageous in chemostats and in other similar fluid systems where similar problems and requirements are experienced. Level control should preferably be accomplished by simple and economical components that do not require the use of an electrical sensor probe or the like but which do coact with a discharge pump to provide for a forced outflow drawn from below the surface of the liquid. Preferably, such a system should not necessarily require perforation of the wall of the liquid containment tank or the like.

The present invention is directed to overcoming one or more of the problems as set forth above.

SUMMARY OF THE INVENTION

In one aspect of the present invention, a fluid system having a vessel which receives an inflow of liquid has a liquid level control which includes a discharge pump for withdrawing liquid from the vessel. The discharge flow intake structure has a branched flow intake path including a first inlet situated above a predetermined liquid level, a second inlet situated below the predetermined liquid level, and a flow junction situated at the predetermined liquid level, the discharge pump being communicated with both of the first and second inlets through the flow junction.

In another specific aspect, the invention is embodied in a chemostat fluid system having a vessel for culturing microorganisms in a liquid medium, inflow means for delivering an inflow of the liquid medium to the vessel, a discharge flow pump having a pumping rate capacity exceeding the rate at which the inflow means delivers the liquid to the vessel, and discharge pump intake means for withdrawing fluid from the vessel. The discharge pump intake means has a branched discharge flow intake path which includes a flow junction in the vessel at a predetermined maximum liquid level and which communicates with the interior of the vessel through a first inlet flow path extending upwardly from the flow junction and also through a second inlet flow path extending downwardly from the flow junction.

If the liquid level in the vessel is below the elevation of the flow junction, the discharge pump aspirates only air or other gas drawn through the upper or first inlet. If the liquid level rises above the level of the flow junction, the discharge pump withdraws liquid through the lower, subsurface second inlet. Thus the liquid level in the vessel is inherently stabilized, at the elevation of the flow junction, by the configuration and location of the discharge flow intake structure. This is accomplished without the use of a complex and costly separate level sensing probe and does not necessarily require that the flow discharge path penetrate through the wall of the vessel. The liquid discharge is forcefully drawn from a location below the surface of the liquid thereby minimizing clogging and adverse effects from substances which may be present at or near the liquid surface.

The invention, together with further objects and advantages thereof, will be better understood by reference to the accompanying drawings and the following description of detailed examples.

BRIEF DESCRIPTION OF THE DRAWINGS

In the accompanying drawings:

FIGS. 3A, 3B and 3C are diagrammatic views of different modes of operation of a discharge pump intake structure utilized in the embodiments of the invention which are depicted in FIGS. 1 and 2.

DETAILED DESCRIPTION OF EMBODIMENTS OF THE INVENTION

Figure 1:
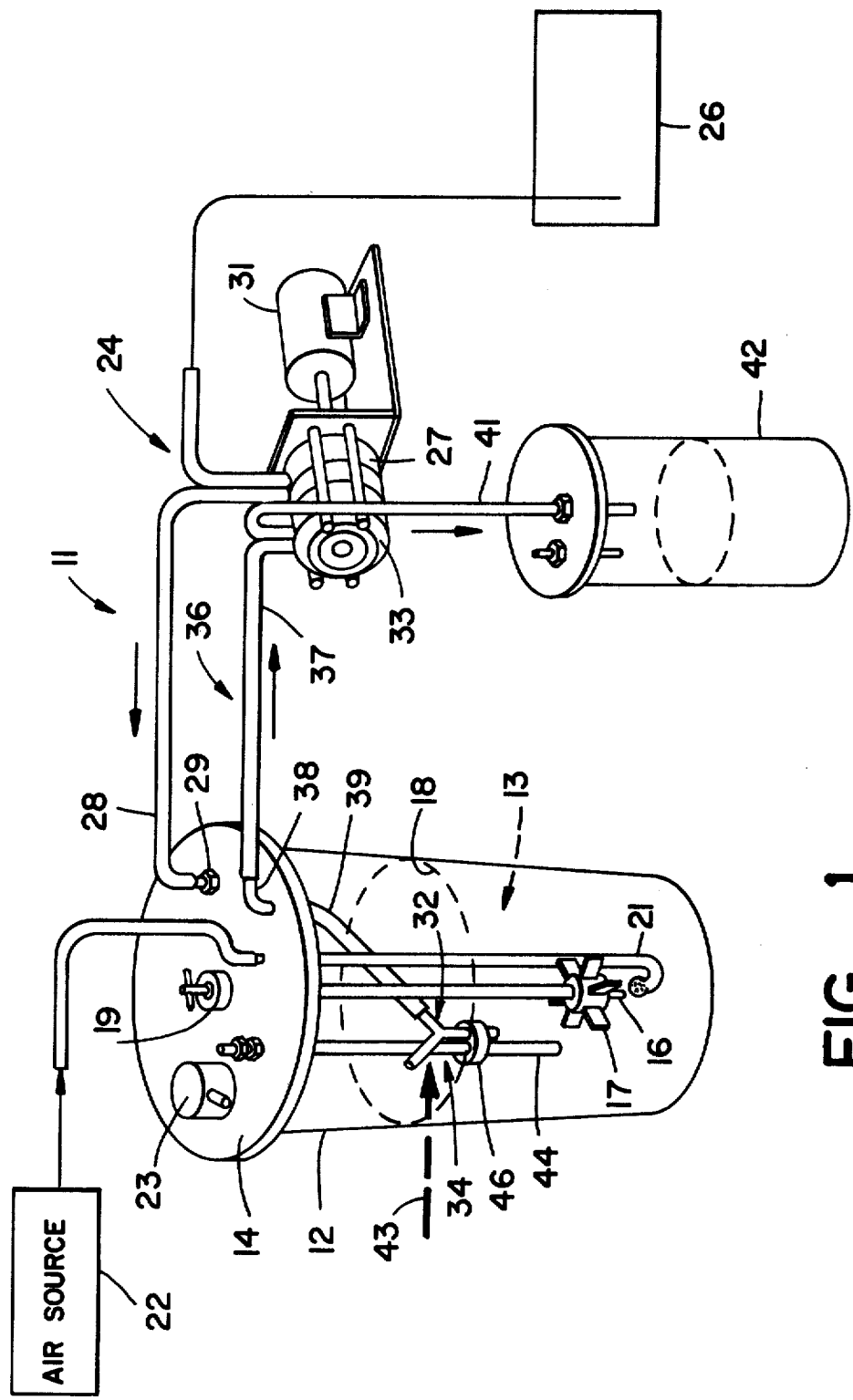
FIG. 1 is a perspective view of an aerobic chemostat in accordance with an embodiment of the invention.

Referring initially to FIG. 1 of the drawings the fluid system 11 of this example is an aerobic chemostat which includes a tank or vessel 12 for containing a liquid 13 in which a microbial culture is maintained, the liquid typically being a solution of nutrients in water. The invention may readily be adapted to other forms of fluid system and to other types of liquid where a predetermined liquid level is to be established and maintained in the presence of an inflow of liquid, turbidostats and chemical or physical reaction equipment being examples. The chemostat vessel 12 has a removable cover 14 which protects the liquid 13 and which also serves to support components of the system 11 that extend into the interior of the vessel. In this particular example, such components include a rotatable stirring rod 16 that extends downward through the cover to a paddle 17 situated below the surface 18 of the liquid 13. The stirring rod 16 and paddle 17 are supported by a bearing 19 at cover 14 which enables motor driven or manual turning of the paddle.

As the chemostat 11 of this example is designed for culturing aerobic microorganisms, an aeration tube 21 receives an airflow from an air source 22 and extends downwardly through cover 14 to a level near the bottom of vessel 12 in order to release the airflow for distribution through the liquid 13. An exhaust fitting 23 provides for discharge of air and gases generated by the microorganisms from the upper region of the vessel 12.

Maintenance of the microbial culture requires a continuous or at least periodic inflow of fresh liquid medium. Supply means 24 for delivering a liquid inflow to vessel 12 for this purpose includes a reservoir 26 of the liquid medium and a supply pump 27 which draws liquid from the reservoir. Supply passage means for delivering the inflow to vessel 12 in this example is a supply hose 28 connected between the pump 27 and an inlet fitting 29 at cover 14. Supply pump 27 may, for example, be of the peristaltic type and is operated by an electrical drive motor 31 in this example.

Because of the inflow of liquid to the vessel 12, liquid level control means 32 are required to avoid overflow and for maintaining the liquid volume in the vessel substantially constant. For this purpose a discharge pump 33 is, in this example, driven by the same drive motor 31 that operates the supply pump 27 and may also be of the peristaltic type. Discharge pump 33 is coupled to discharge flow intake structure 34 situated within the vessel 12 through discharge passage means 36 which in the present example includes a discharge flow hose 37 connected between the discharge pump and an additional fitting 38 at cover 14, the fitting 38 being coupled to intake structure 34 through an additional length of hose 39 situated within the vessel. Still another hose 41 delivers the outflow from discharge pump 33 to a vented effluent receiving tank 42.

To prevent a rise of the liquid surface 18 above the predetermined desired level, the discharge pump 33 and discharge passage means 36 have a maximum discharge flow rate pumping capacity which exceeds the rate of inflow of liquid to the vessel 12. This may be provided for in any of several ways. In the present embodiment the supply pump 27 and discharge pump 33 are identical and are driven at the same speed by a single motor 31. To provide for a discharge flow rate which may exceed the inflow rate, at least one component of the inflow path is sized to cause the inflow path to have greater flow resistance than the discharge flow path. In particular, in this example, supply hose 28 has a smaller inside diameter than discharge flow hose 37. Other forms of flow constriction in the inflow path may be used in other instances. It is also possible to provide for a maximum discharge flow exceeding the inflow rate by using a separate discharge pump driven at a higher speed than the supply pump 27 is driven or by using a discharge pump which is larger than the supply pump.

The configuration and placement of the discharge flow intake structure 34 provides for maintaining the surface 18 of the liquid within vessel 12 at a predetermined desired level which is diagrammatically indicated in FIG. 1 by dashed horizontal arrow 43. To support the intake structure 34 at the desired location, a mounting rod 44 extends downward from cover 14 and the intake structure is fixed to the rod by suitable means, such as a plastic band 46 or adhesive coated tape. Adjustment of the vertical position of the intake structure 34, and thus the liquid level, is possible by vertical movement of the mounting rod 44.

Referring now to FIG. 3A, the discharge flow intake structure 34 defines a branched discharge flow intake path 47 which includes a first inlet 48 situated above the predetermined desired liquid level 43, a second inlet 49 situated below the predetermined liquid level and a flow junction 51 situated at the predetermined liquid level, the discharge pump 33 being communicated with both of the inlets 48 and 49 through the flow junction 51. More specifically, in this particular example, the discharge flow intake structure 34 is a Y-shaped integral element having a first tubulation 53 extending upward from level 43 to define the first inlet flow path and having a second tubulation 54 extending downward from the level 43 to define the second inlet flow path. The intake structure 34 has a third tubulation 56 extending upward from the predetermined level at an angle with respect to the first tubulation to communicate discharge pump 33 with the flow junction 51 defined by the junction of the three tubulations 53, 54, 56 and which is situated at the predetermined level 43.

Where a layer 57 of thick scum, or floating particulate matter tends to form at the top of the liquid volume 13, the second tubulation 54 extends downward into the liquid a distance exceeding the maximum thickness of the surface layer 57 to situate the submerged second inlet 49 below the surface layer 57. First tubulation 53 extends up a distance sufficient to locate the first inlet 48 above any light foam that may form above the surface 18.

Figure 2:
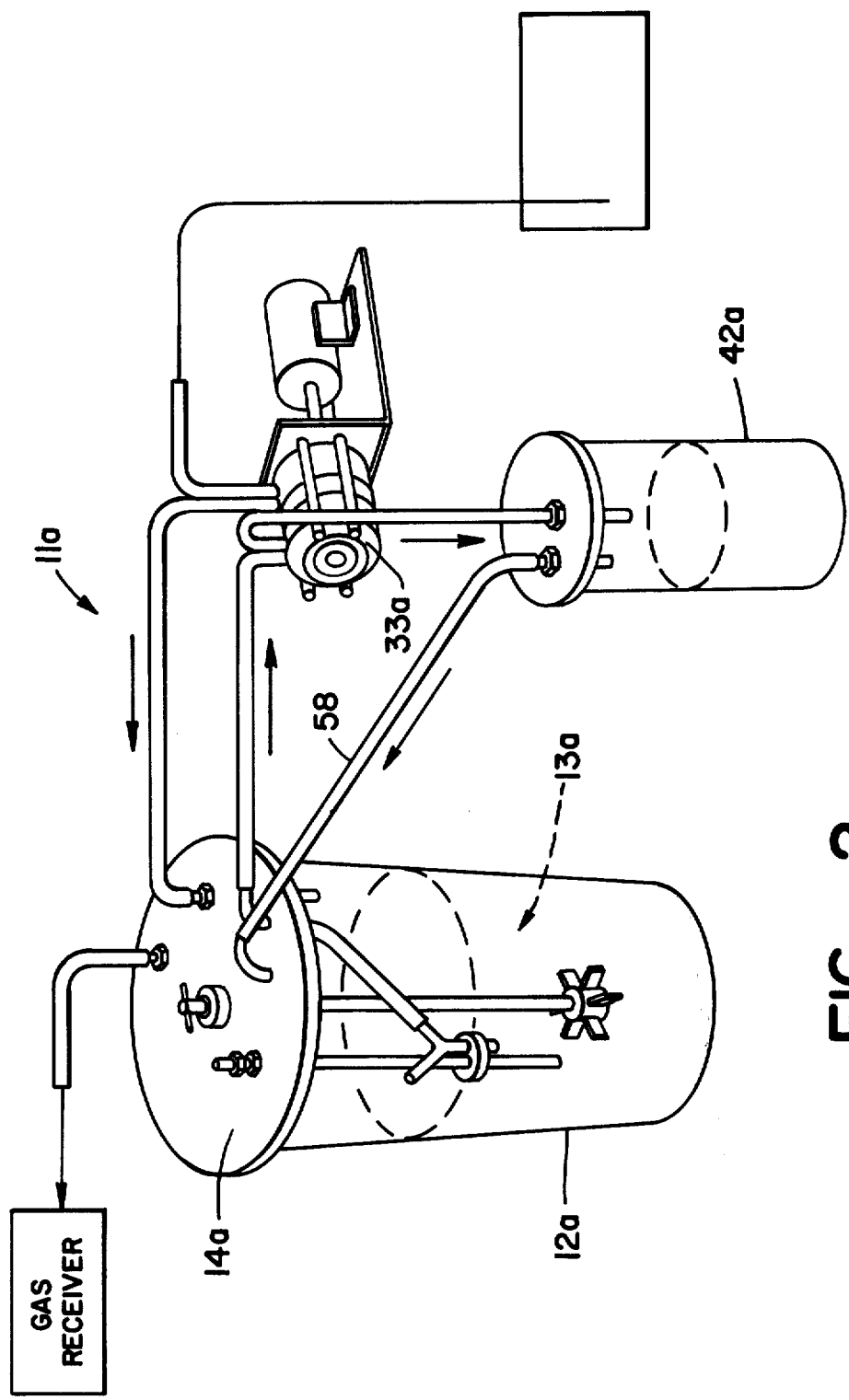
FIG. 2 is a perspective view of an anaerobic chemostat in accordance with another embodiment of the invention.

Referring to FIG. 2, the invention is readily adaptable to closed or unvented fluid systems such as an anaerobic chemostat 11a in which microorganisms are cultured in the absence of free oxygen. Much of the structure of the anaerobic chemostat 11a may be similar to that of the embodiment of FIG. 1 and accordingly need not be redescribed. The anaerobic chemostat 11a differs from the previously described embodiment in that the air source 22, air inlet tube 21 and air vent 23 of the embodiment of FIG. 1 are not present. In the anaerobic chemostat of FIG. 2, the cover 14a seals the top of vessel 12a in order to maintain a volume of oxygen free gas within the region above the liquid volume 13a. The gas may be air depleted of its oxygen content by the microorganisms, an introduced gas that is compatible with anaerobic microorganisms or gases produced by the life processes of the microorganisms.

As will be described in connection with operation of the system, a flow of gas from the region above liquid 13a is withdrawn from the vessel 12a by the discharge pump 33a. To maintain the gaseous atmosphere in the top region of vessel 12a, the effluent receiving tank 42a is closed rather than being vented as in the previously described embodiment and a gas return hose 58 communicates the upper region of effluent receiving tank 42a with the upper region of vessel 12a.

OPERATION

In operation, with reference again to FIG. 1, the vessel 12 may be initially filled with the liquid medium 13 to the desired level 43 and the microbial culture which is to be maintained may be introduced into the liquid through the feed inlet fitting 29 for example, by temporarily disconnecting supply hose 28. After replacement of the supply hose 28, air source 22 may be activated to aerate the liquid at a desired rate. Drive motor 31 is also actuated to cause supply pump 27 to deliver an inflow of fresh liquid medium into the vessel 12. Actuation of the drive motor 31 also operates discharge pump 33 which then draws an outflow of liquid, gas or a mixture of liquid and gas from the vessel 12 depending on the relationship of the surface 18 of the liquid to predetermined level 43, the outflow being delivered to effluent receiving tank 42.

Owing to the configuration and placement of the discharge flow intake structure 34 this outflow is inherently regulated to stabilize the surface 18 of the liquid 13 in vessel 12 at predetermined level 43. This effect may best be understood by referring to FIGS. 3A, 3B and 3C. Referring first to FIG. 3A in particular, the discharge flow intake structure 34 is positioned so that the flow junction 51 defined by the confluence of first, second and third tubulations 53, 54 and 56 straddles the predetermined desired liquid level 43. If the liquid surface 18 is initially below predetermined level 43 then the discharge flow 55 to pump 33 consists of air or other gas aspirated from the region above the liquid through first inlet 48. Consequently the surface 18 of the liquid 13 will rise owing to the previously described inflow of liquid into the vessel.

Referring now to FIG. 3B, if the liquid surface 18 is initially above predetermined level 43, the discharge flow 55 to pump 33 consists of liquid drawn through the second submerged inlet 49 and through tubulation 54. As the discharge system components are sized to cause a discharge flow rate exceeding the rate of inflow of liquid, liquid surface 18 is then lowered until it has dropped to the predetermined level 43.

FIG. 3C depicts the stabilized condition at which liquid surface 18 is maintained at the predetermined level 43 by balancing of the opposing effects discussed above with reference to FIGS. 3A and 3B. Under the stabilized condition depicted in FIG 3C, the discharge flow 55 is a mixture of gas and liquid with the liquid component being just sufficient to compensate for the inflow of new liquid into the vessel. When the liquid surface 18 starts to rise incrementally above level 43, the proportion of liquid in the discharge flow 55 increases and the surface is returned to the predetermined level. If the liquid surface 18 starts to recede incrementally from level 43, the proportion of liquid in the discharge flow decreases allowing the liquid surface to be restored to the predetermined level 43. Thus the outflow of liquid 13 is automatically matched to liquid inflow.

One specific example of a chemostat 11 of the form depicted in FIG. 1 included a 14 liter vessel 12 containing a volume of liquid 13 which was varied between 4 and 10 liters at different stages of operation and which included culture suspended solids of up to 0.6 g/L. The discharge flow inlets 48, 49 and tubulations 53, 54, 56 had an internal diameter of 0.6 cm. Liquid inflow to vessel 12 from supply pump 27 was varied from 1 L/day up to 44 L/day during a series of microorganism culturing experiments which lasted for a period of up to 8 weeks each. Liquid level was maintained within ±0.25 cm and clogging of the tubulations did not occur.

In the chemostatic embodiments of the invention described herein, the controlled liquid level is the interface between a liquid and a gas. As will be apparent, the apparatus may be used to control the level of the interface between two immiscible liquids of different density in systems in which there is an inflow of liquid.

While the invention has been described with respect to certain specific embodiments, many variations are possible and it is not intended to limit the invention except as defined in the following claims.

We claim:

1. In a fluid system having a vessel which receives an inflow of liquid and having a liquid level control for maintaining a predetermined liquid level in the vessel and which includes a discharge pump for withdrawing liquid from said vessel, the improvement comprising:

discharge flow intake structure having a branched discharge flow intake path which includes a first inlet situated above said predetermined liquid level, a second inlet situated below said predetermined liquid level, and a flow junction situated at said predetermined liquid level, said pump being communicated with both of said first and second inlets through said flow junction, wherein said liquid in said vessel has a surface layer with a composition differing from that of the subjacent volume of said liquid in said vessel, wherein said second inlet of said discharge flow intake structure is situated below said surface layer and within said subjacent volume of said liquid, wherein said discharge flow intake structure includes a first tubulation extending upwardly from said flow junction and having an opening above said flow junction constituting said first inlet, a second tubulation extending downwardly from said flow junction and having an opening below said flow junction constituting said second inlet, and a third tubulation extending upwardly from said flow junction at an angle with respect to said first tubulation to communicate said flow junction with said discharge pump.

2. A fluid system as set forth in claim 1 further including means for delivering an inflow of said liquid to said vessel at a predetermined inflow rate, wherein said discharge pump and said discharge flow intake structure have a discharge flow rate pumping capacity exceeding said predetermined rate of said inflow of said liquid into said vessel.

3. A fluid system as set forth in claim 1 further including a flow conduit communicating said flow junction with said discharge pump and wherein at least the portion of said flow conduit which is closest to said junction extends upwardly therefrom.

4. A fluid system as set forth in claim 1 further including a source of said liquid, a supply pump connected between said source and said vessel to deliver said inflow of liquid thereto, and a drive motor coupled to both said supply pump and said discharge pump.

5. A fluid system as set forth in claim 4 further including inflow passage means for delivering said liquid from said supply pump to said vessel, and discharge passage means which includes said discharge flow intake structure for transmitting fluid from said vessel to said discharge pump, said discharge passage means being proportioned to have less flow resistance than said supply passage means.

6. A fluid system as set forth in claim 1 wherein said fluid system is a chemostat for culturing microorganisms in said liquid within said vessel and wherein the volume of said liquid therein exhibits a surface layer of scum, said discharge flow intake structure being proportioned and positioned to situate said first inlet above said surface layer in spaced apart relationship therefrom and to situate said second inlet below said surface layer in spaced relationship therefrom.

7. A fluid system as set forth in claim 6 wherein said vessel is closed and wherein said predetermined liquid level in said vessel is at an intermediate level therein providing for a volume of gas above the volume of said liquid therein, further including a closed effluent reservoir connected to said discharge pump to receive said discharge flow therefrom and a gas return conduit communicating the upper region of said effluent reservoir with said vessel.

8. A chemostat fluid system having a vessel for culturing microorganisms in a liquid medium, inflow means for delivering an inflow of said liquid medium to said vessel, a discharge flow pump having a pumping rate capacity exceeding the rate at which said inflow means delivers said liquid medium to said vessel, and discharge pump intake structure for withdrawing fluid from said vessel, said intake structure having a branched discharge flow intake path which includes a flow junction in said vessel at a predetermined maximum liquid level therein and which communicates with the interior of said vessel through a first inlet flow path extending upward from said flow junction and also through a second inlet flow path extending downward from said flow junction, wherein said liquid in said vessel has a surface layer with a composition differing from that of the subjacent volume of said liquid in said vessel, wherein said second inlet of said discharge flow intake structure is situated below said surface layer and within said subjacent volume of said liquid, wherein said discharge flow intake structure includes a first tubulation extending upwardly from said flow junction and having an opening above said flow junction constituting said first inlet, a second tubulation extending downwardly from said flow junction and having an opening below said flow junction constituting said second inlet, and a third tubulation extending upwardly from said flow junction at an angle with respect to said first tubulation to communicate said flow junction with said discharge pump.

9. A chemostat fluid system as defined in claim 8 wherein said discharge flow intake structure is communicated with said discharge flow pump through a flow path which extends upward from said intake structure and out of said vessel at the top thereof.

10. A chemostat fluid system as defined in claim 8 wherein said discharge flow intake structure is mounted on a support which extends downward into said vessel from the top thereof and which is disengagable from said vessel.

* * * * *